(12) United States Patent
Sauer et al.

(10) Patent No.: US 10,433,869 B2
(45) Date of Patent: *Oct. 8, 2019

(54) PERCUSCOPIC ACCESS DEVICE AND CLEANING OBTURATOR

(71) Applicant: LSI Solutions, Inc., Victor, NY (US)

(72) Inventors: Jude S. Sauer, Pittsford, NY (US); Angelo John Martellaro, Victor, NY (US)

(73) Assignee: LSI Solutions, Inc., Victor, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/849,045

(22) Filed: Dec. 20, 2017

(65) Prior Publication Data

US 2018/0110541 A1 Apr. 26, 2018

Related U.S. Application Data

(63) Continuation of application No. 15/366,707, filed on Dec. 1, 2016, now Pat. No. 9,993,265.

(Continued)

(51) Int. Cl.
*A61B 17/34* (2006.01)
*A61B 90/70* (2016.01)
(Continued)

(52) U.S. Cl.
CPC ...... *A61B 17/3421* (2013.01); *A61B 1/00135* (2013.01); *A61B 1/121* (2013.01);
(Continued)

(58) Field of Classification Search
CPC . A61F 13/38; A61B 17/3421; A61B 17/3417; A61B 17/3423; A61B 90/70;
(Continued)

(56) References Cited

U.S. PATENT DOCUMENTS 6,126,592 A 10/2000 Proch
8,566,995 B2 10/2013 Asano
(Continued)

OTHER PUBLICATIONS

Mar. 3, 2016 Web Page; http://www.kapitex.com/tracheostomy/essentials/trachi-swab;Trachi-Swab.
Sep. 25, 2017 Office Action; from U.S. Appl. No. 15/366,707.

*Primary Examiner* — Pedro Philogene
*Assistant Examiner* — David C Comstock
(74) *Attorney, Agent, or Firm* — David J. Gervasi; Christopher B. Miller

(57) ABSTRACT

A percuscopic access device is disclosed. The percuscopic access device has a hollow shaft with a proximal opening and a distal opening. The percuscopic access device also has one or more barrier ridges on the outside of the hollow shaft. The percuscopic access device also has one or more recesses on the inside of the hollow shaft and in communication with the distal opening. A cleaning obturator for use with the percuscopic access device is also disclosed. The cleaning obturator and percuscopic access device may be combined as a surgical apparatus. The cleaning obturator has a guide rod having a proximal end and a distal end. The cleaning obturator also has a plugging tip on the distal end. The cleaning obturator further has one or more swab guides proximal to the plugging tip.

16 Claims, 17 Drawing Sheets

Related U.S. Application Data

(60) Provisional application No. 62/261,854, filed on Dec. 1, 2015.

(51) Int. Cl.
*A61B 17/02* (2006.01)
*A61F 13/38* (2006.01)
*A61B 1/00* (2006.01)
*A61B 1/12* (2006.01)
*A61B 17/00* (2006.01)
*A61B 90/00* (2016.01)

(52) U.S. Cl.
CPC ...... *A61B 17/0218* (2013.01); *A61B 17/3417* (2013.01); *A61B 17/3423* (2013.01); *A61B 90/70* (2016.02); *A61F 13/38* (2013.01); *A61B 90/361* (2016.02); *A61B 2017/00942* (2013.01); *A61B 2017/3437* (2013.01); *A61B 2017/3484* (2013.01)

(58) Field of Classification Search
CPC ........ A61B 90/361; A61B 2017/00942; A61B 2017/3437; A61B 2017/3484
USPC ....... 600/204, 104, 114, 119, 127, 128, 129, 600/130, 131, 155
See application file for complete search history.

(56) References Cited

U.S. PATENT DOCUMENTS

| | | |
|---|---|---|
| 8,821,383 B2 | 9/2014 | Mirza |
| 8,827,893 B2 | 9/2014 | Mirza |
| 9,402,531 B2 | 8/2016 | Chin |
| 9,993,265 B2 * | 6/2018 | Sauer ................ A61B 90/70 |
| 2006/0253102 A1 | 11/2006 | Nance et al. |
| 2007/0270766 A1 | 11/2007 | Kucklick |
| 2009/0105543 A1 | 4/2009 | Miller |
| 2016/0331406 A1 | 11/2016 | Chin |

* cited by examiner

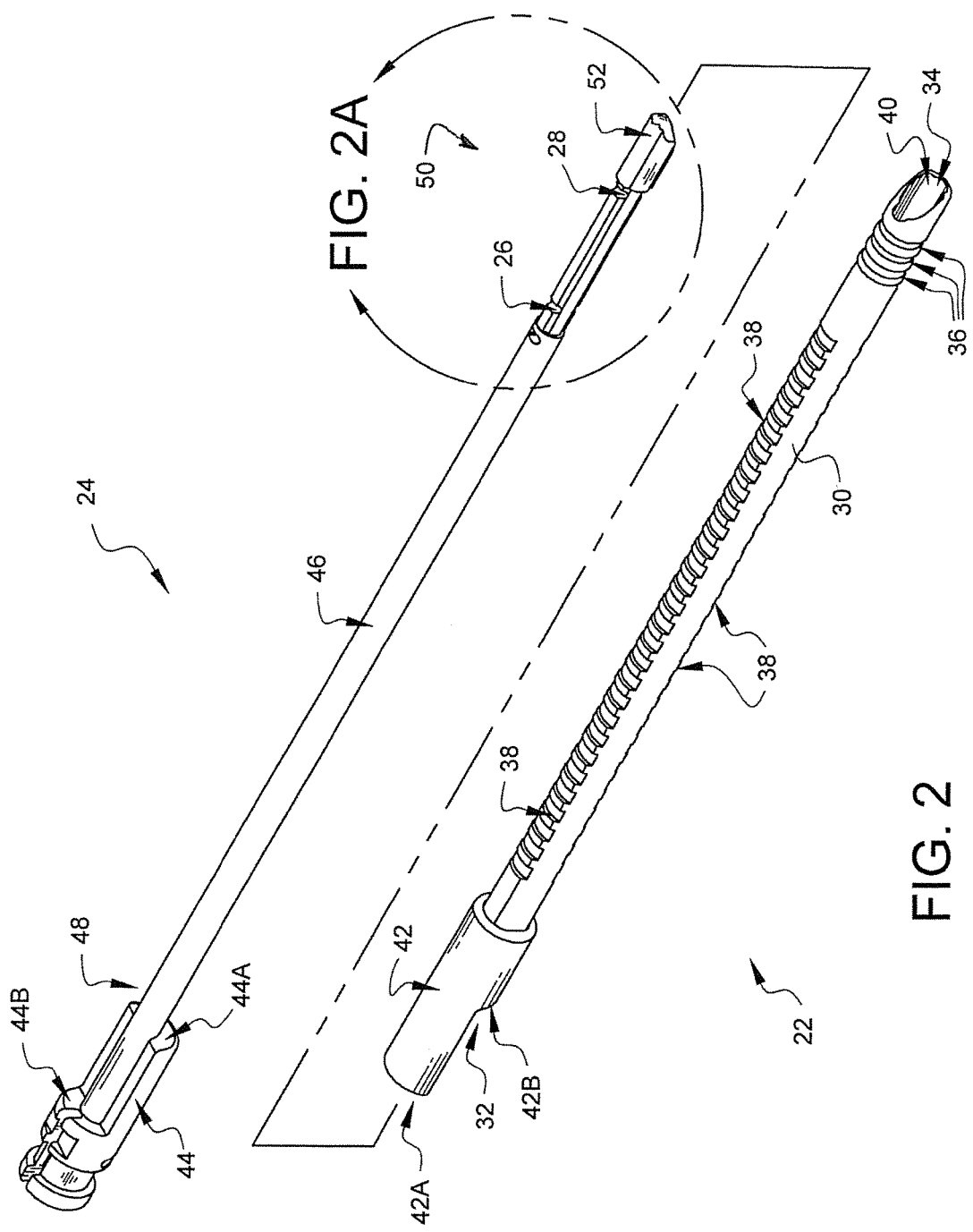

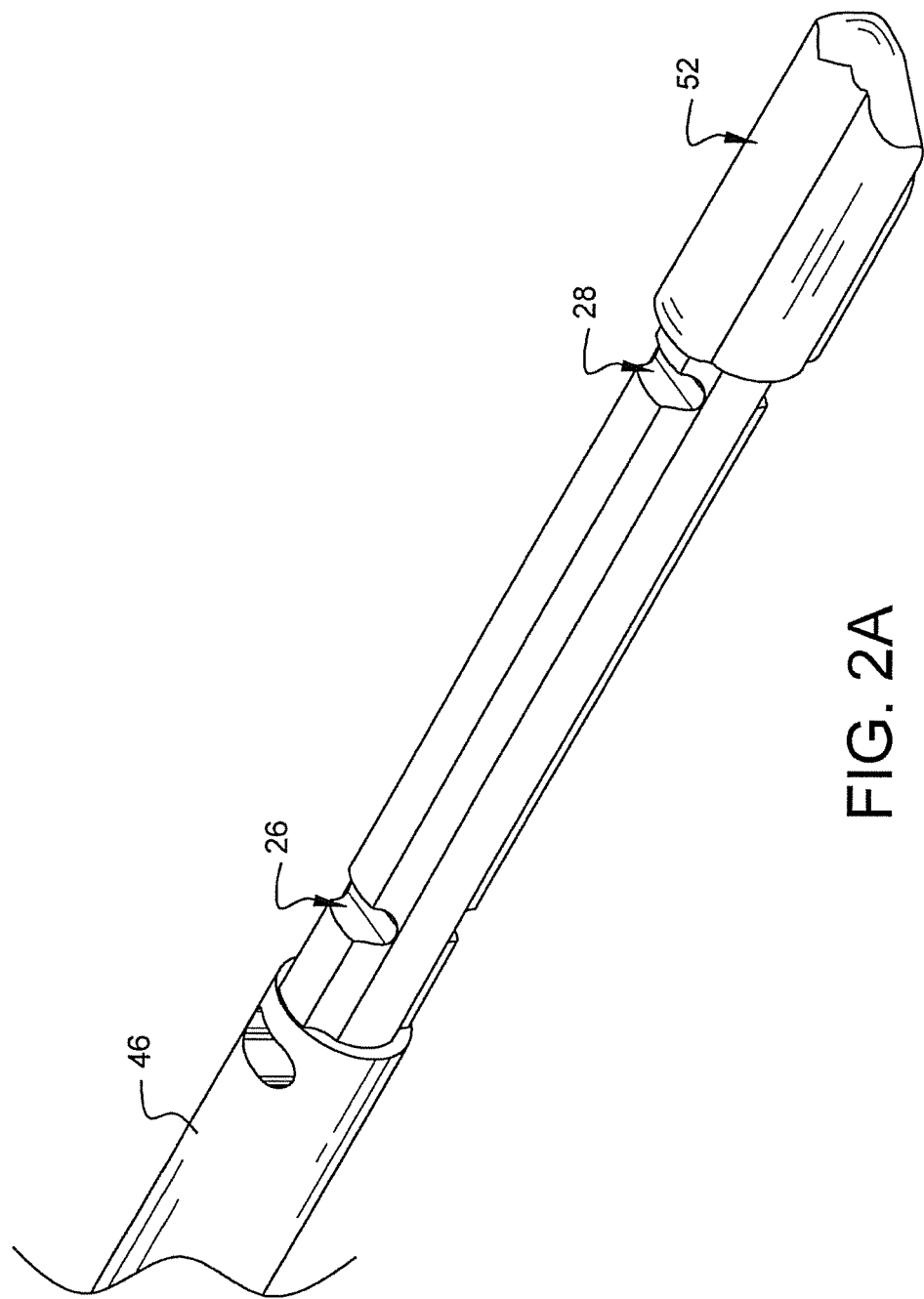

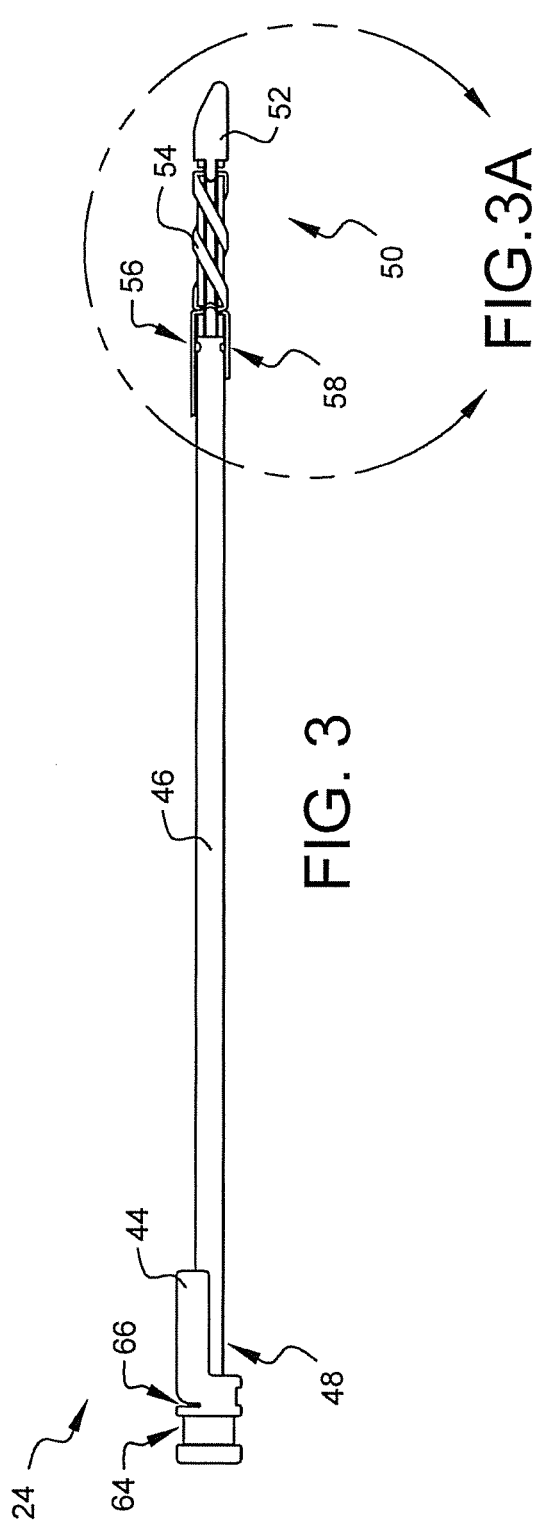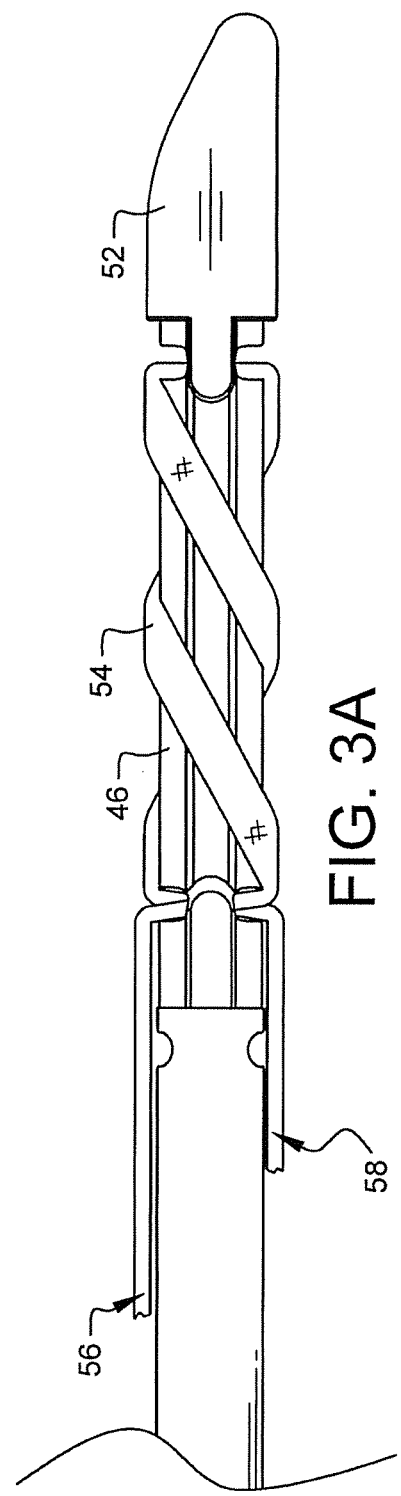

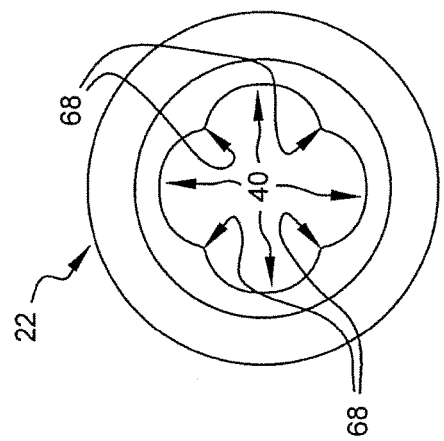
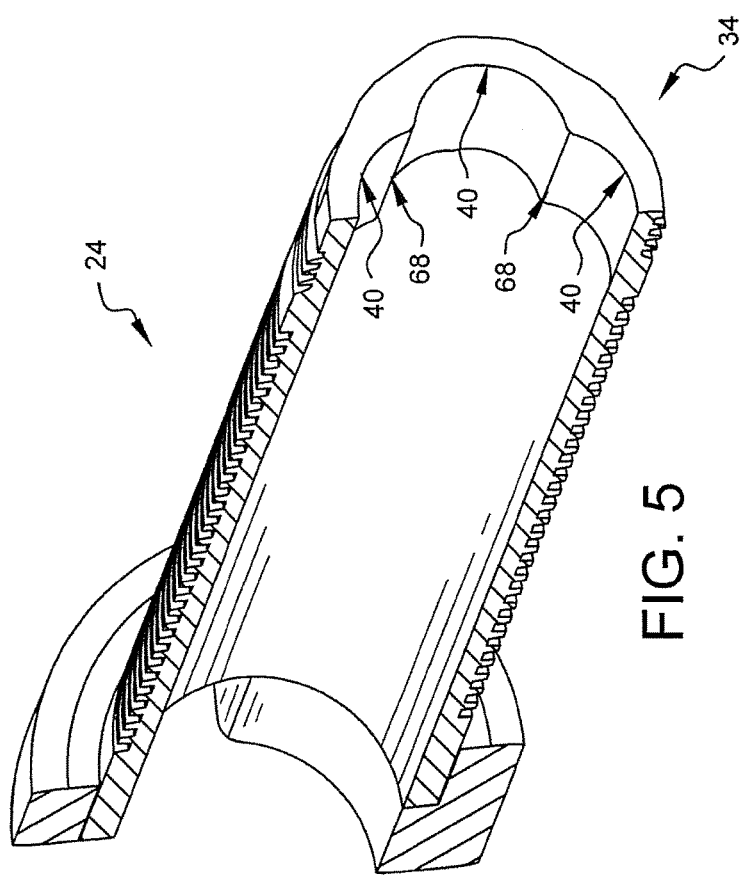

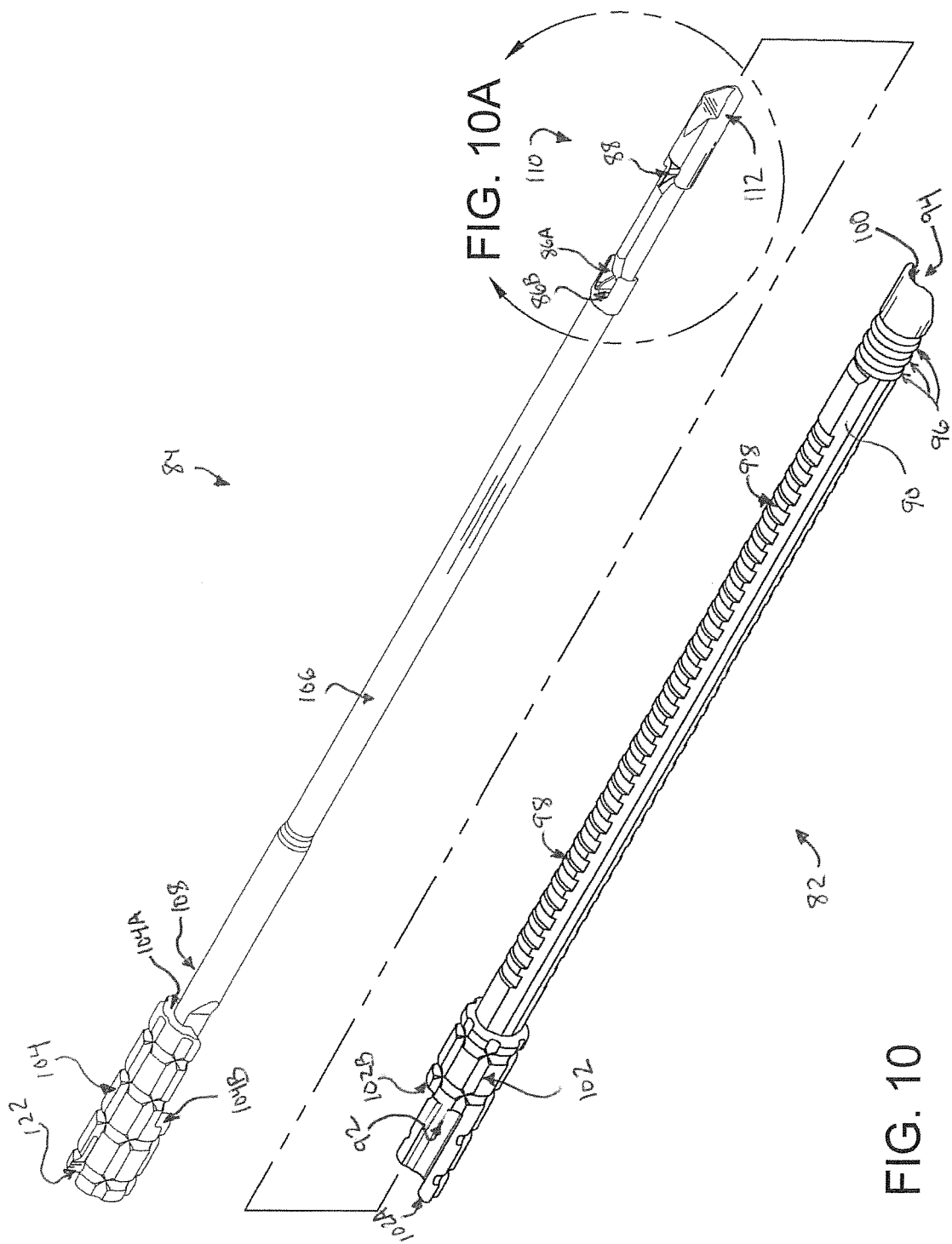

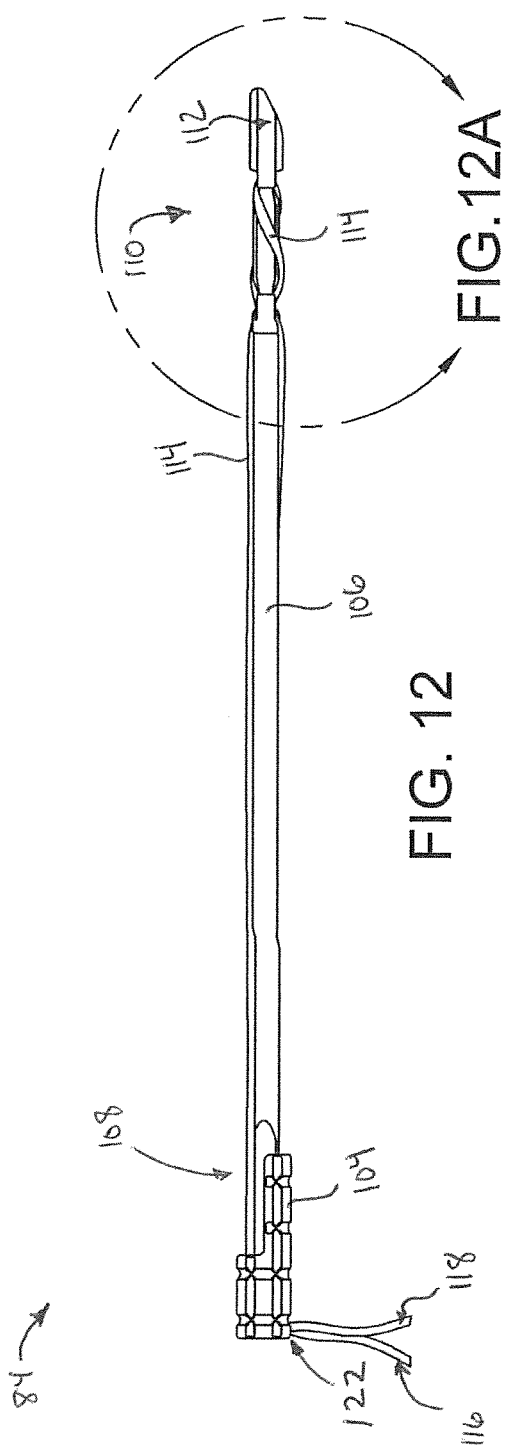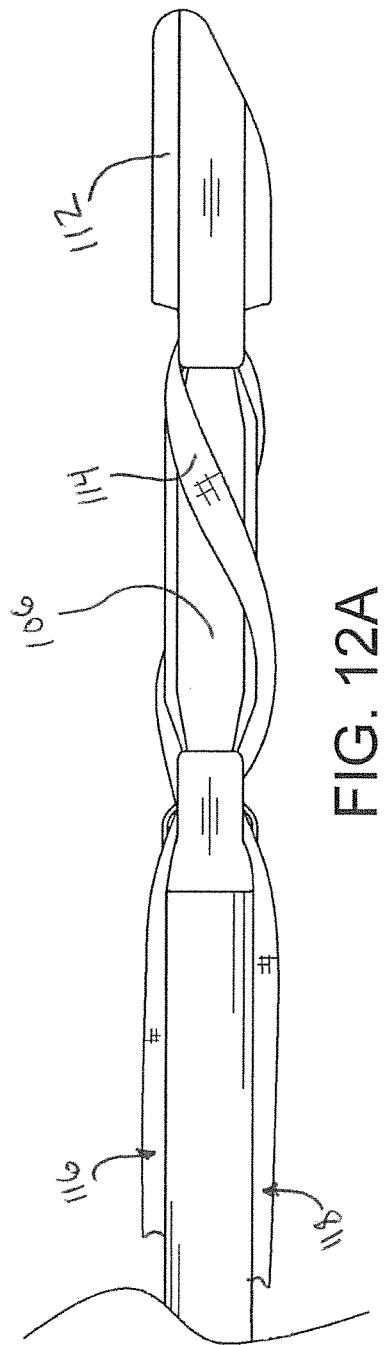

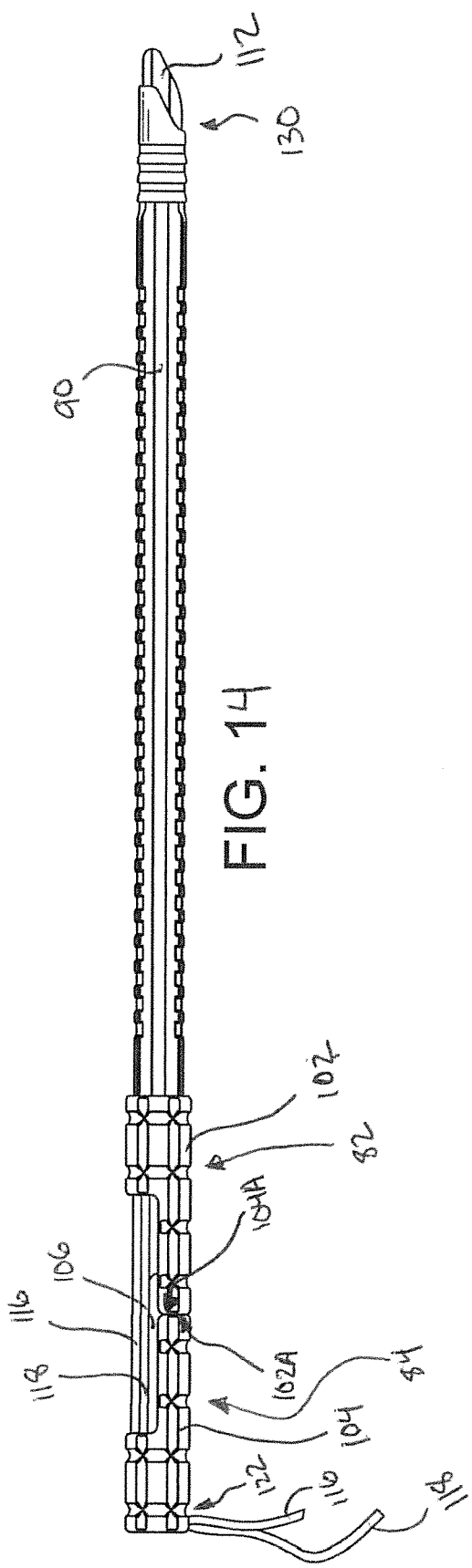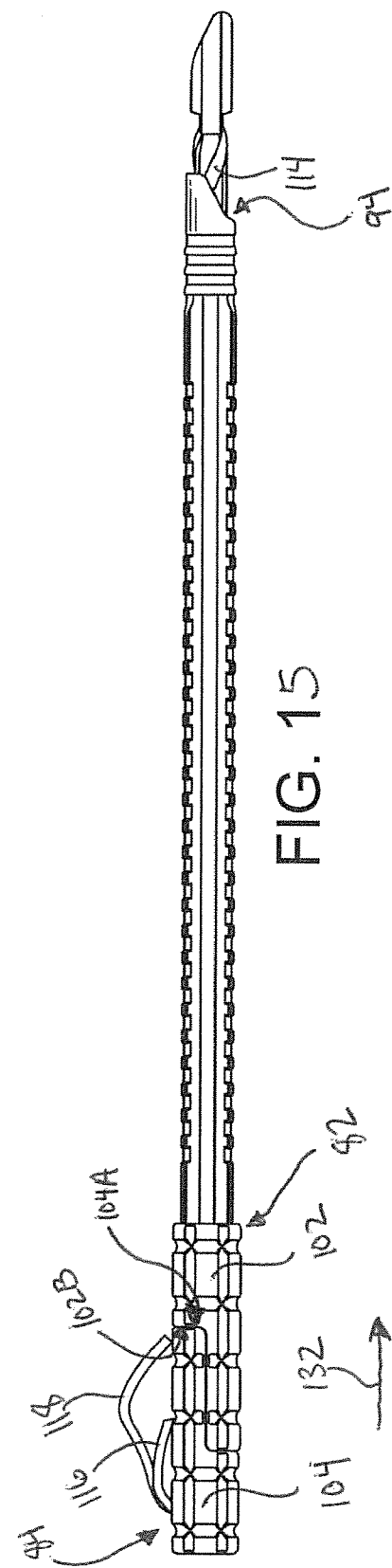

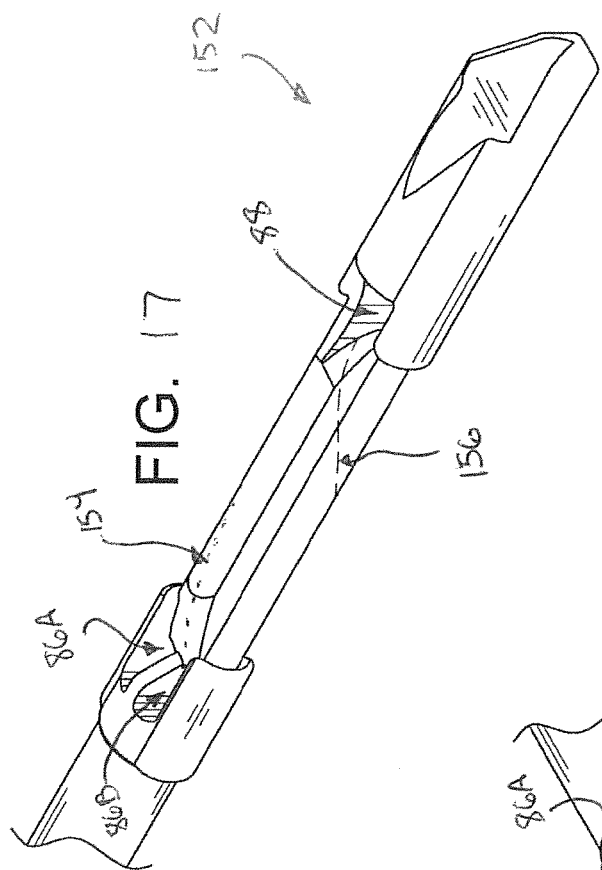
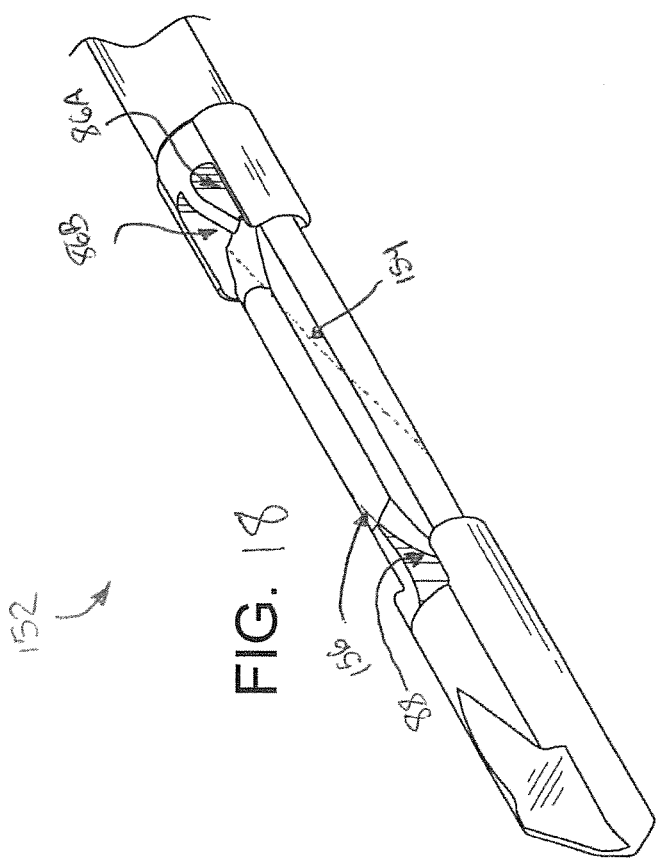

PERCUSCOPIC ACCESS DEVICE AND CLEANING OBTURATOR

RELATED APPLICATION

This application claims priority to U.S. Provisional Patent Application No. 62/261,854, filed Dec. 1, 2015, and entitled, "PERCUSCOPIC ACCESS DEVICE AND CLEANING OBTURATOR".

FIELD

The claimed invention relates to surgical devices, and more specifically to a surgical scope port that may be used in conjunction with a cleaning obturator.

BACKGROUND

Laparoscopic, endoscopic, and other types of minimally invasive surgical procedures often rely on percutaneous introduction of a viewing scope into an internal region of a patient where the surgical procedure is to be performed. Providing such access for a viewing scope may be referred to as providing "percuscopic" access. The viewing scope may be any type of laparoscope, endoscope, or other imaging device known to those skilled in the art. The viewing scope is commonly introduced through an access tube, such as a cannula, which is passed into the patient's chest through a small incision strategically placed by a surgeon. By inserting a viewing scope through the cannula, the surgeon can view the region to be treated on an imaging monitor and can perform a variety of surgical procedures using specialized surgical instruments which are introduced through one or more other access tubes or cannulas. Viewing scopes may be used in a wide variety of surgical procedures, including, but not limited to cardiac valve repair or replacement.

Unfortunately, when providing percuscopic access for a viewing scope, problems can arise whereby bodily fluids, which naturally come into contact with the end of the cannula inserted into the patient, can foul the lens of a viewing scope that has been inserted therein.

Therefore, it would be desirable to have a device for providing percuscopic access that is capable of reducing contact of a viewing scope inserted therein with fluids and/or other materials which would tend to foul the lens. It would also be desirable to have a convenient and effective device for removing fluids and/or other materials from a percuscopic access device to reduce the likelihood that the fluid could foul a viewing scope lens inserted therein.

SUMMARY

A percuscopic access device is disclosed. The percuscopic access device has a hollow shaft with a proximal opening and a distal opening. The percuscopic access device also has one or more barrier ridges on the outside of the hollow shaft. The percuscopic access device also has one or more recesses on the inside of the hollow shaft and in communication with the distal opening.

A cleaning obturator for use with the percuscopic access device is also disclosed. The cleaning obturator and percuscopic access device may be combined as a surgical apparatus. The cleaning obturator has a guide rod having a proximal end and a distal end. The cleaning obturator also has a plugging tip on the distal end. The cleaning obturator further has one or more swab guides proximal to the plugging tip.

BRIEF DESCRIPTION OF THE DRAWINGS

FIG. 2 is an exploded perspective view of the percuscopic access device and the cleaning obturator of FIG. 1.

FIG. 2A is an enlarged perspective view of the distal end of the cleaning obturator of FIG. 2.

FIG. 3 is a side view of one embodiment of the cleaning obturator of FIG. 2A.

FIG. 3A is an enlarged side view of the distal end of the cleaning obturator of FIG. 3.

FIG. 5 is a distal perspective cross-sectional view of the percuscopic access device of FIG. 4.

FIG. 6 is a distal elevational view of the percuscopic access device of FIG. 4.

FIG. 10 is an exploded perspective view of the percuscopic access device and the cleaning obturator of FIG. 9.

FIG. 12 is a side view of one embodiment of the cleaning obturator of FIG. 10A.

FIG. 12A is an enlarged side view of the distal end of the cleaning obturator of FIG. 12.

FIGS. 14 and 15 are side views which illustrate two phases of interaction between the percuscopic access device of FIG. 13 and the cleaning obturator of FIG. 11.

FIGS. 17 and 18 are perspective views of another embodiment of a distal end of a cleaning obturator.

Figure 1:
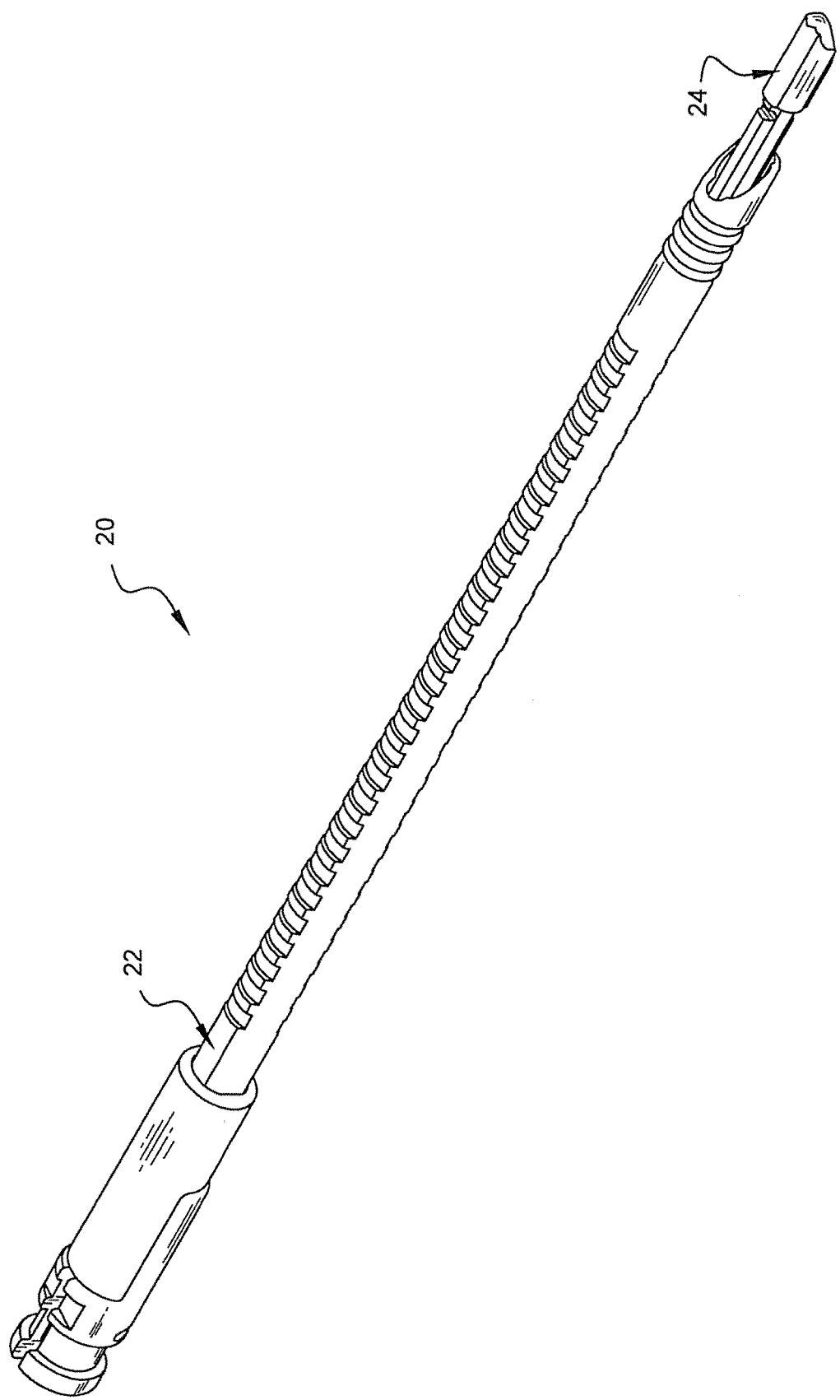
FIG. 1 is a perspective view of one embodiment of a percuscopic access device with a cleaning obturator.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

FIG. 1 is a perspective view of one embodiment of a surgical device 20. The device 20 has a percuscopic access device 22 and a cleaning obturator 24. The percuscopic access device 22 is configured to slideably receive the cleaning obturator 24 through an opening in its proximal end, as may be seen more clearly in the exploded view of FIG. 2. The cleaning obturator 24 has one or more swab guides 26, 28 which may be configured to slideably receive a swab. The swab is not shown in FIGS. 1 and 2 so that underlying structures may more clearly be seen, however, the swab will be shown and discussed in more detail with regard to later FIGS. 3, 3A, 7, and 8.

Referring to FIG. 2 again, the percuscopic access device 22 has a hollow shaft 30 with a proximal opening 32 and a distal opening 34. In this embodiment, the hollow shaft 30 has at least a partially beveled end where the distal opening 34 is located. In addition to being configured to slideably receive the cleaning obturator 24, the hollow shaft 30 is also configured to receive a viewing scope entering the proximal opening 32 and positionable at the distal opening 34 to allow a surgeon to obtain images of a surgical area of interest. The percuscopic access device 22 also has one or more barrier ridges 36 on the outside of the hollow shaft 30. The barrier ridges 36 are configured to catch fluid drips and reduce the likelihood that those drips will flow all the way down to the distal opening 34 where they can potentially foul a lens of a viewing scope that has been placed into the percuscopic access device 22. This embodiment of the percuscopic access device 22 further has one or more textured features 38 on the outside of the hollow shaft 30. The textured features 38 allow easy insertion of the percuscopic access device 22 into an incision as well as reasonably easy repositioning while precluding inadvertent slip out of the percuscopic access device 22 from the incision site.

In this embodiment, the barrier ridges 36 are located distal to the one or more textured features 38, adjacent to the distal opening 34. In other embodiments, the barrier ridges could be completely or partially surrounded by the textured features. In this embodiment, the barrier ridges 36 fully encircle the hollow shaft 30, but in other embodiments, one or more of the barrier ridges may be less than a full circle. The barrier ridges 36 may be formed from the same continuous material as the hollow tube 30, for example by machining, turning, molding, deposition, or other suitable fabrication methods known to those skilled in the art. In other embodiments, the barrier ridges 36 may be formed from a separate material which is coupled to the hollow tube 30, for example by welding, gluing, press fitting, clamping, or other suitable fastening methods known to those skilled in the art.

Depending on the embodiment, the barrier ridges 36 may be recessed with respect to the outside of the hollow shaft 30, protrude with respect to the outside of the hollow shaft 30, be flush with respect to the outside of the hollow shaft 30, or any combination thereof. The barrier ridges 36 may have a profile that takes advantage of Van der Waals forces to increase the likelihood of hydrostatic attraction overcoming gravitational forces which are acting on fluids which contact the percuscopic access device 22. Additionally, some embodiments may have one or more barrier ridges which comprise a hydrophilic material and/or which have a hydrophilic coating to increase fluid attraction, thereby further reducing the likelihood that unwanted fluids will foul a lens of a viewing scope placed within the percuscopic access device 22.

The percuscopic access device 22 also has one or more recesses 40 on the inside of the hollow shaft 30 and in communication with the distal opening 34. These recesses 40 will be discussed in more detail later with regard to FIGS. 5 and 6.

Referring to FIG. 2 again, the percuscopic access device 22 also has a phased handle 42 for interacting with a complementary phased handle 44 of the cleaning obturator 24. The term "phased handle" refers to the fact that the two handles may be rotated relative to each other between two different positions or phases to enable different functionality when the obturator 24 is engaged within the percuscopic access device 22. These different "phases" will be discussed in more detail later with regard to FIGS. 7 and 8. The phased handle 42 of the percuscopic access device 22 has a first interface 42A and a second interface 42B. The phased handle 44 of the cleaning obturator 24 has a first interface 44A and a second interface 44B.

As shown in FIG. 2, the cleaning obturator 24 has a guide rod 46 having a proximal end 48 and a distal end 50. The guide rod 46 may include complementary features which allow the guide rod 46 to slide easily within the hollow shaft 30 of the percuscopic access device 22. A plugging tip 52 is located at the distal end 50 of the guide rod 46. As will be shown later, the plugging tip 52 may be positioned in one of the handle 42, 44 engagement phases such that the plugging tip 52 seals or at least reduces the likelihood that fluids will enter the percuscopic access device 22 from the distal opening 34. In this embodiment, the plugging tip 52 is beveled, but other embodiments may have plugging tips with other shapes. As mentioned previously, the cleaning obturator 24 also includes one or more swab guides 26, 28 proximal to the plugging tip 52.

Figure 2B:
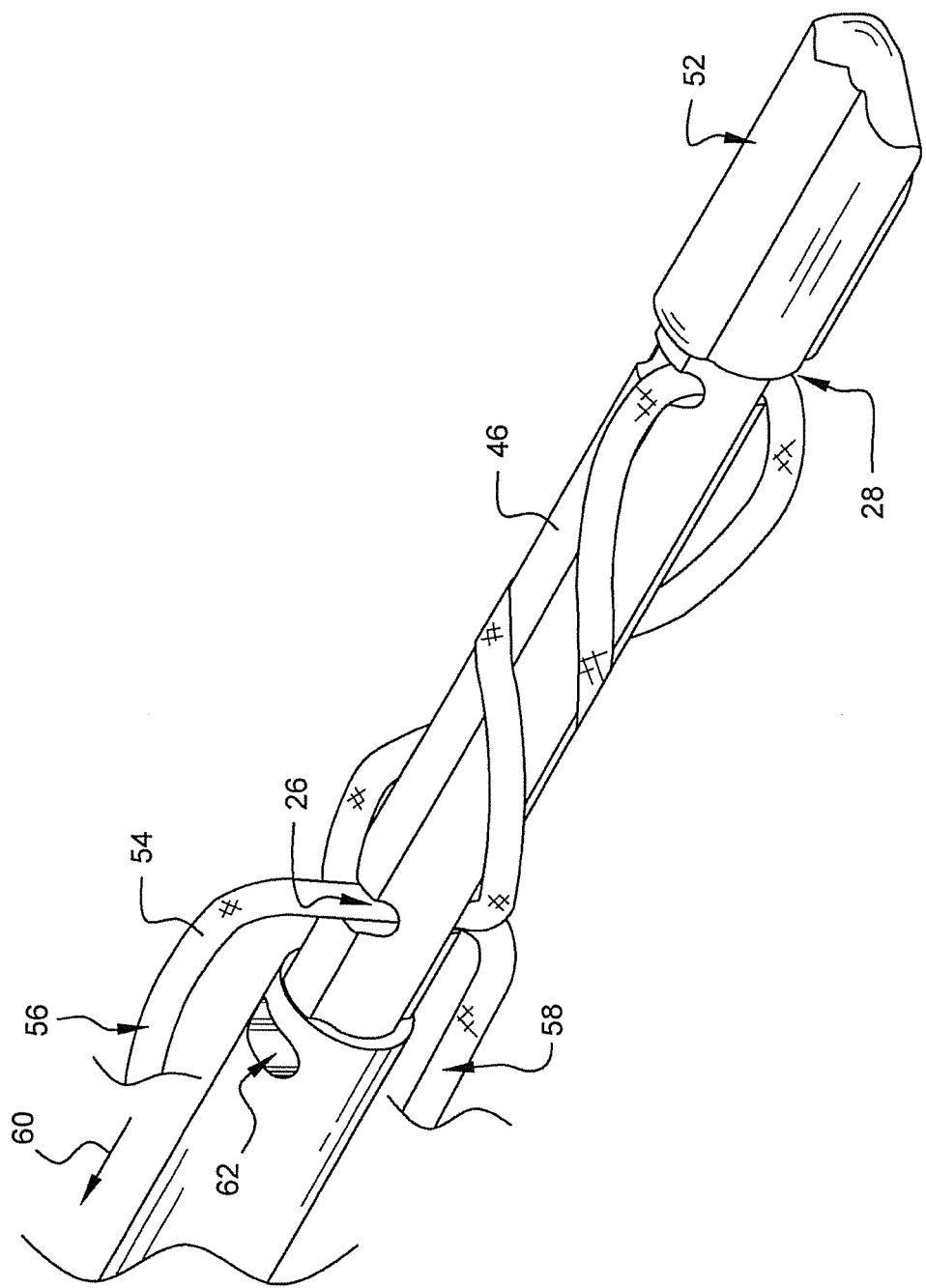
FIG. 2B is an enlarged perspective view of the distal end of the cleaning obturator of FIG. 2A with one embodiment of a cleaning swab installed on the cleaning obturator.

The swab guides 26, 28 may be seen more clearly in the enlarged view of FIG. 2A. In this embodiment, the swab guides 26, 28 are holes which pass through the guide rod 46. The swab guides 26, 28 are configured to receive a swab (not shown in FIG. 2A). There are many different ways a swab could engage the swab guides 26, 28, but one possible embodiment is illustrated in FIG. 2B, where a swab 54, comprising a length of umbilical tape in this example, is passed down through the swab guide 26, wrapped around the guide rod 46 towards the swab guide 28, passed up through the swab guide 28, wrapped back around the guide rod 46 towards the swab guide 26, and then passed down, again, through the swab guide 26. The ends of the swab 56, 58 may be routed along the guide rod 46 towards the phased handle 44 (not visible in this view). Although the swab 54 is shown in relatively loose engagement with the guide rod 46 (in order to make it easier to follow the path of the swab 54), one or more of the ends 56, 58 may be cinched to cause the swab 54 to fit more closely with the guide rod 46.

Although the swab 54 is illustrated as passing at least 360 degrees around the guide rod 46, other embodiments may have swabs which cover a greater or lesser portion of the guide rod 46. Although not a strict requirement, a substantially spiral or helical type path is advantageous over a cylindrical swab because it creates less friction with the inner walls of the percuscopic access device 22. This can make it easier to slide and maneuver the cleaning obturator 24 within the percuscopic access device 22.

As will be discussed in more detail later in this specification, the swab 54 is moved relative to the percuscopic access device 22 to clean the distal opening 34 so that a viewing scope inserted into the percuscopic access device 22 is not as likely to get fouled by bodily fluids present in the surgical area. With a wrapped swab 54 configuration like the one illustrated in FIG. 2B, one end of the swab (either end 56 or end 58) may advantageously be pulled in a proximal direction 60 (or other direction) to cause a previously used portion of the swab to move past the area between the swab guides 26, 28 and be replaced by a clean portion of the swab 54 to improve/refresh/extend the cleaning capacity of the cleaning obturator 24. The end of the swab which is pulled may include a pull coupled to the swab to make it easier to grasp. The pull may also be configured to help a user thread the swab 54 through the one or more swab guides 26, 28 when first setting up the swab 54 on the guide rod 46.

In the example of FIG. 2B, both ends 56, 58 of the swab 54 pass through the swab guide 26. While this helps the resultant swab helixes be more symmetrical, in other embodiments it may be desirable to avoid passing the swab more than once through a swab guide. In that case, an additional swab guide 62 may be provided in the guide rod 46, and one of the ends 56, 58 may pass through swab guide 62 instead of through swab guide 26 a second time.

FIG. 3 illustrates the cleaning obturator 24 in a side view. The swab 54 can be seen wrapped around the distal end 50 of the guide rod 46, proximal to the plugging tip 52. FIG. 3A shows this in enlarged detail. The ends 56, 58 of the swab 54 are shown truncated for simplicity, but as will be seen in later views, the suture ends 56, 58 may pass along the guide rod 46 and be wrapped around a spool portion 64 of the phased handle 44, where the ends 56, 58 can then be pulled into groove 66 to hold them steady, if desired.

Figure 4:
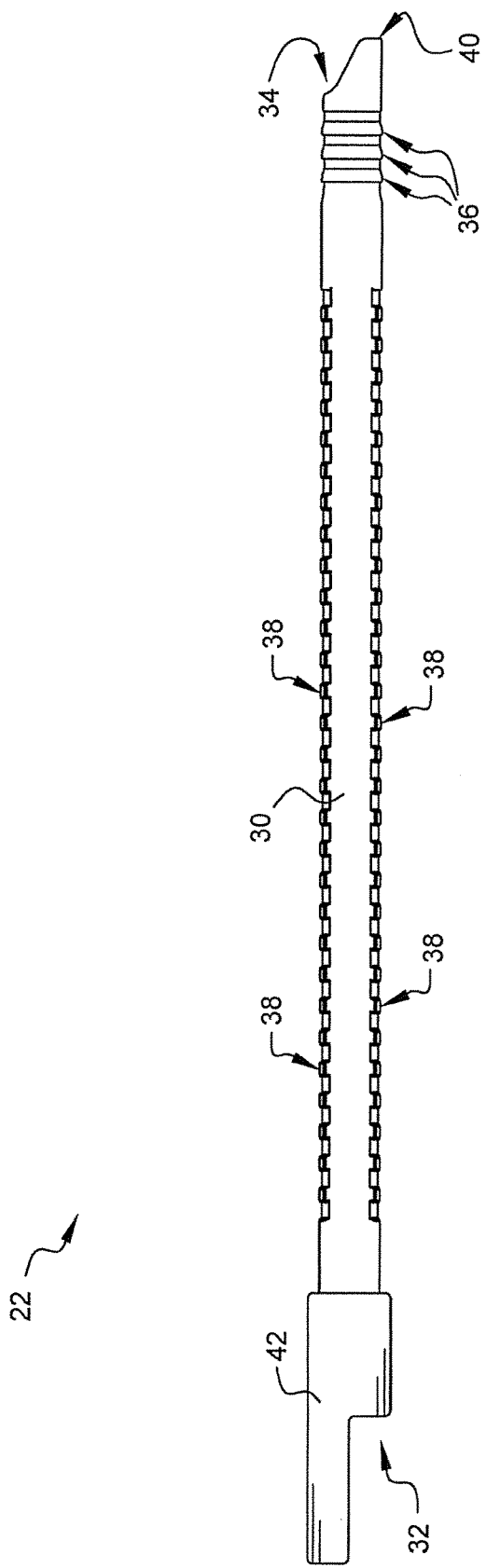
FIG. 4 is a side view of the percuscopic access device of FIG. 2.

FIG. 4 illustrates the percuscopic access device 22 in a side view. Many features of the percuscopic access device 22 have been discussed above. However, the one or more recesses 40 on the inside of the hollow shaft 30, in communication with the distal opening 34 can be described in more detail. Examples of the recesses 40 may be seen more clearly in the enlarged perspective sectioned view of FIG. 5, which looks at the percuscopic access device 22 from a distal perspective. The end elevational view of FIG. 6 may also be helpful for visualizing the recesses 40. The protrusions 68 which help to define or delineate between each of the recesses 40 are intended to keep a viewing scope that has been passed into the percuscopic access device 22 from coming into contact with the recesses 40. The recesses 40 provide further areas where unwanted fluid may accumulate without contacting or fouling the scope lens. In some embodiments, the recesses 40 may include a hydrophilic coating. The protrusions 68 may be substantially longitudinal protrusions, but they do not necessarily need to extend all the way through the percuscopic access device 22. In some embodiments, where the longitudinal protrusions 68 may include a ramped transition from an inside diameter of the shaft 30 to a smaller effective diameter where movement of the viewing scope is more limited by the protrusions 68 near the distal opening 34.

Figure 7:
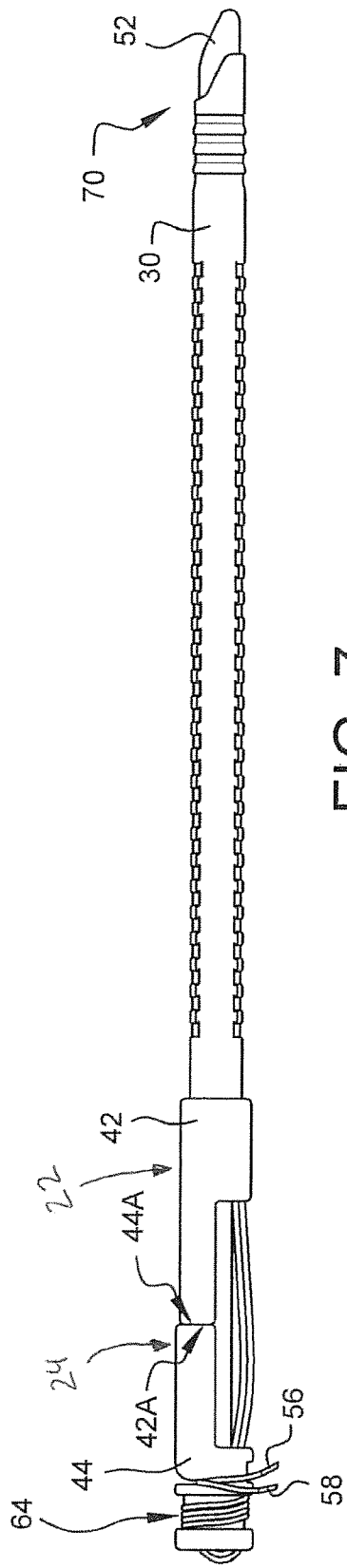
FIGS. 7 and 8 are side views which illustrate two phases of interaction between the percuscopic access device of FIG. 4 and the cleaning obturator of FIG. 2B.
Figure 8:
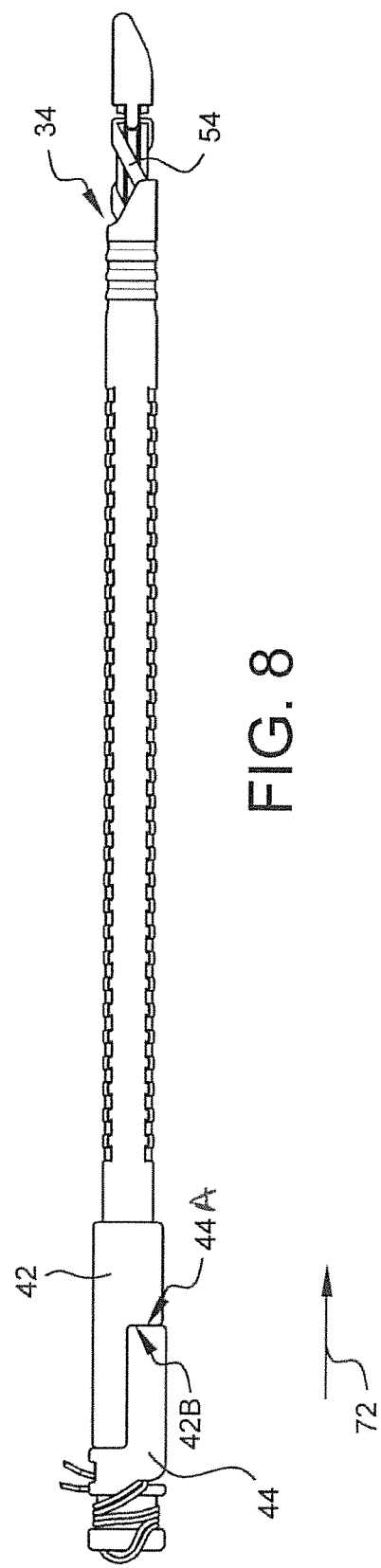

FIGS. 7 and 8 are side views which illustrate two phases of interaction between the percuscopic access device 22 and the cleaning obturator 24. In FIG. 7, the cleaning obturator 24 has been inserted into the percuscopic access device 22 such that the first interface 42A of the percuscopic access device phased handle 42 is in contact with the first interface 44A of the cleaning obturator phased handle 44. In this position, or phase, the plugging tip 52 is sealing the hollow shaft 30 of the percuscopic access device 22. Although not visible in FIG. 7, the swab 54 is wrapped around the distal end of the cleaning obturator 24 as discussed previously, and the swab ends 56, 58 are wrapped around a spool portion 64 of the phased handle 44 to help hold the swab 54 in place and/or to help keep the ends of the swab 56, 58 organized and out of the way. As configured in FIG. 7, the distal end 70 of the assembly may be inserted into an incision in a patient. The narrow size and atraumatic profile of the assembly are intended for minimizing iatrogenic intercostal tissue space trauma and to maintain hemostasis.

Once the distal end 70 of the assembly has been inserted into the patient, the phased handle 44 of the cleaning obturator 24 is rotated 180 degrees around a longitudinal axis, causing the first interface 44A of the cleaning obturator phased handle 44 to disengage from the first interface 42A of the percuscopic access device phased handle 42. The phased handle 44 of the cleaning obturator 24 may then be pushed in a distal direction 72 until the first interface 44A of the cleaning obturator phased handle 44 contacts the second interface 42B of the percuscopic access device phased handle 42 as shown in FIG. 8. This causes the swab 54 to clean out the distal opening 34 of the percuscopic access device 22 so that fluids do not enter this optical space. Ideally, but not necessarily, the distance along the guide rod 46 for a 360 degree wrap of the swab 54 is less than or equal to the distance the guide rod 46 travels relative to the percuscopic access device 22 when the cleaning obturator 24 is moved into the position shown in FIG. 8. This will ensure that all edges of the distal opening 34 have a chance to be cleaned.

The cleaning obturator 24 may then be removed from the percuscopic access device 22, and a viewing scope may be inserted therein. If, at any time, it is desired to clean the percuscopic access device 22 again, the viewing scope (not shown) may be removed from the percuscopic access device 22 and the cleaning obturator 24 may be inserted again as shown in FIG. 8. Additionally, the swab 54 may be advanced, as discussed above, to present a clean swab surface to the distal opening 34 for any of the ensuing cleanings.

Figure 9:
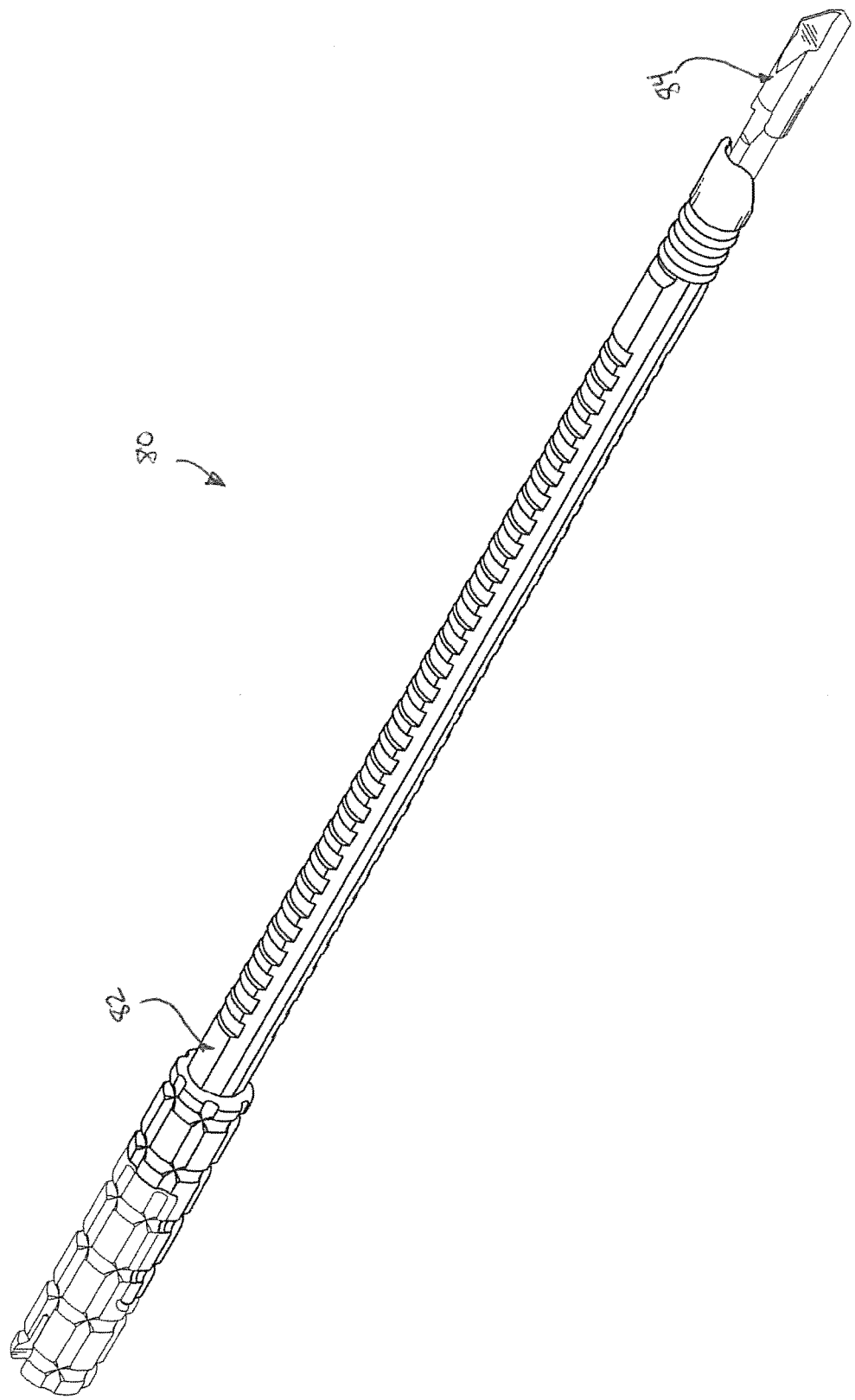
FIG. 9 is a perspective view of another embodiment of a percuscopic access device with a cleaning obturator.

FIG. 9 is a perspective view of another embodiment of a surgical device 80. The device 80 has a percuscopic access device 82 and a cleaning obturator 84. The percuscopic access device 82 is configured to slideably receive the cleaning obturator 84 through an opening in its proximal end, as may be seen more clearly in the exploded view of FIG. 10. The cleaning obturator 84 has one or more swab guides 86A, 86B, 88 which may be configured to slideably receive a swab. The swab is not shown in FIGS. 9 and 10 so that underlying structures may more clearly be seen, however, the swab will be shown and discussed in more detail with regard to later FIGS. 11, 12, and 12A.

Referring to FIG. 10 again, the percuscopic access device 82 has a hollow shaft 90 with a proximal opening 92 and a distal opening 94. In this embodiment, the hollow shaft 90 has at least a partially beveled end where the distal opening 94 is located. In addition to being configured to slideably receive the cleaning obturator 84, the hollow shaft 90 is also configured to receive a viewing scope entering the proximal opening 92 and positionable at the distal opening 94 to allow a surgeon to obtain images of a surgical area of interest. The percuscopic access device 82 also has one or more barrier ridges 96 on the outside of the hollow shaft 90. The barrier ridges 96 are configured to catch fluid drips and reduce the likelihood that those drips will flow all the way down to the distal opening 94 where they can potentially foul a lens of a viewing scope that has been placed into the percuscopic access device 82. This embodiment of the percuscopic access device 82 further has one or more textured features 98 on the outside of the hollow shaft 90. The textured features 98 allow easy insertion of the percuscopic access device 82 into an incision as well as reasonably easy repositioning while precluding inadvertent slip out of the percuscopic access device 82 from the incision site.

In this embodiment, the barrier ridges 96 are located distal to the one or more textured features 98, adjacent to the distal opening 94. In other embodiments, the barrier ridges could be completely or partially surrounded by the textured features. In this embodiment, the barrier ridges 96 fully encircle the hollow shaft 90, but in other embodiments, one or more of the barrier ridges may be less than a full circle. The barrier ridges 96 may be formed from the same continuous material as the hollow tube 90, for example by machining, turning, molding, deposition, or other suitable fabrication methods known to those skilled in the art. In other embodiments, the barrier ridges 96 may be formed from a separate material which is coupled to the hollow tube 90, for example by welding, gluing, press fitting, clamping, or other suitable fastening methods known to those skilled in the art.

Depending on the embodiment, the barrier ridges 96 may be recessed with respect to the outside of the hollow shaft 90, protrude with respect to the outside of the hollow shaft 90, be flush with respect to the outside of the hollow shaft 90, or any combination thereof. The barrier ridges 96 may have a profile that takes advantage of Van der Waals forces to increase the likelihood of hydrostatic attraction overcoming gravitational forces which are acting on fluids which contact the percuscopic access device 82. Additionally, some embodiments may have one or more barrier ridges which comprise a hydrophilic material and/or which have a hydrophilic coating to increase fluid attraction, thereby further reducing the likelihood that unwanted fluids will foul a lens of a viewing scope placed within the percuscopic access device 82.

The percuscopic access device 82 also has one or more recesses 100 on the inside of the hollow shaft 90 and in communication with the distal opening 94. Such recesses have been discussed above with regard to the embodiments of FIGS. 5 and 6.

Referring to FIG. 10 again, the percuscopic access device 82 also has a phased handle 102 for interacting with a complementary phased handle 104 of the cleaning obturator 84. The term "phased handle" refers to the fact that the two handles may be rotated relative to each other between two different positions or phases to enable different functionality when the obturator 84 is engaged within the percuscopic access device 82. These different "phases" will be discussed in more detail later with regard to FIGS. 14 and 15. The phased handle 102 of the percuscopic access device 82 has a first interface 102A and a second interface 102B. The phased handle 104 of the cleaning obturator 84 has a first interface 104A and a second interface 104B.

As shown in FIG. 10, the cleaning obturator 84 has a guide rod 106 having a proximal end 108 and a distal end 110. The guide rod 106 may include complementary features which allow the guide rod 106 to slide easily within the hollow shaft 90 of the percuscopic access device 82. A plugging tip 112 is located at the distal end 110 of the guide rod 106. As will be shown later, the plugging tip 112 may be positioned in one of the handle 102, 104 engagement phases such that the plugging tip 112 seals or at least reduces the likelihood that fluids will enter the percuscopic access device 82 from the distal opening 94. In this embodiment, the plugging tip 112 is beveled, but other embodiments may have plugging tips with other shapes. As mentioned previously, the cleaning obturator 84 also includes one or more swab guides 86A, 86B, 88 proximal to the plugging tip 112.

Figure 10A:
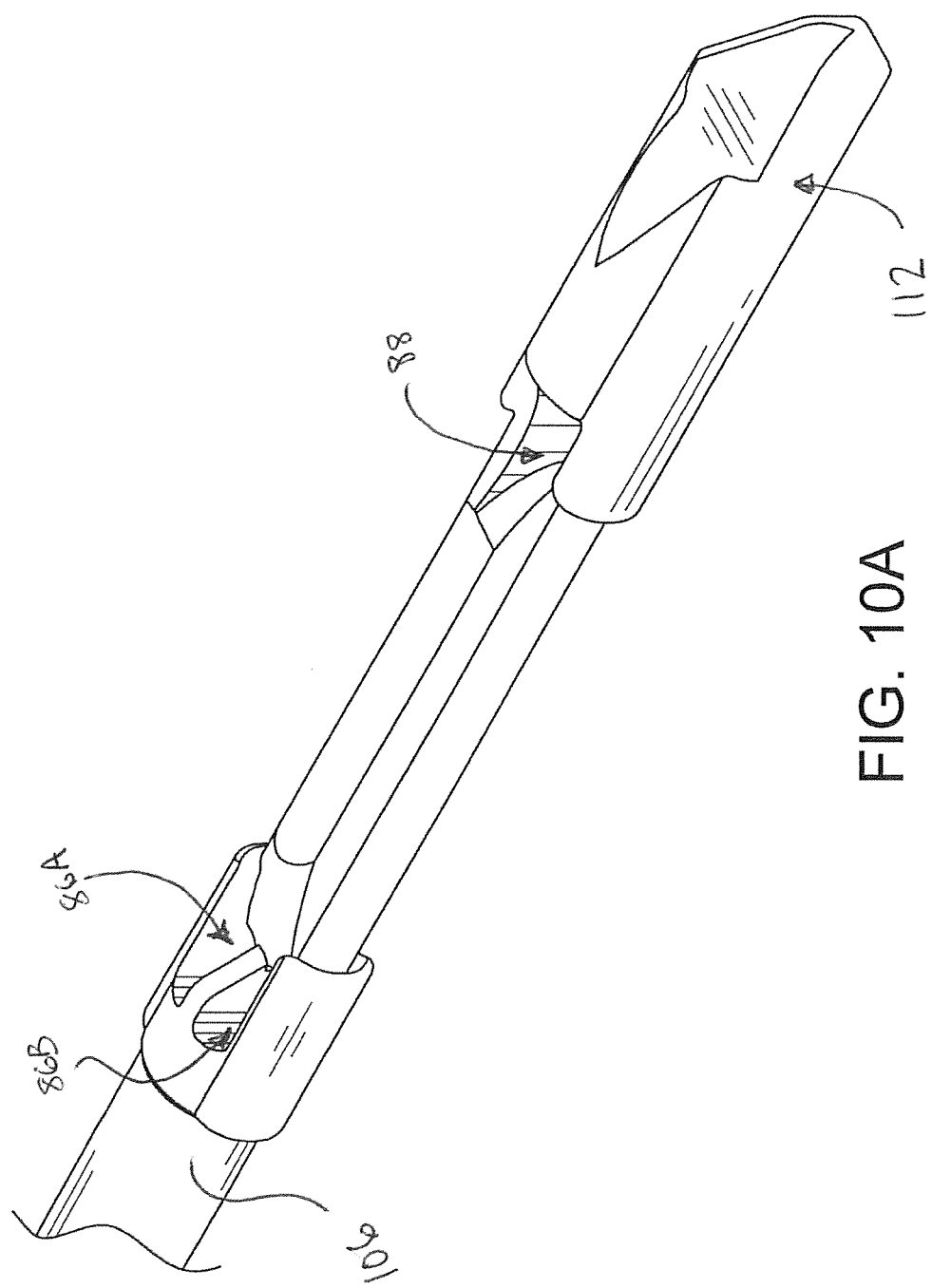
FIG. 10A is an enlarged perspective view of the distal end of the cleaning obturator of FIG. 10.
Figure 11:
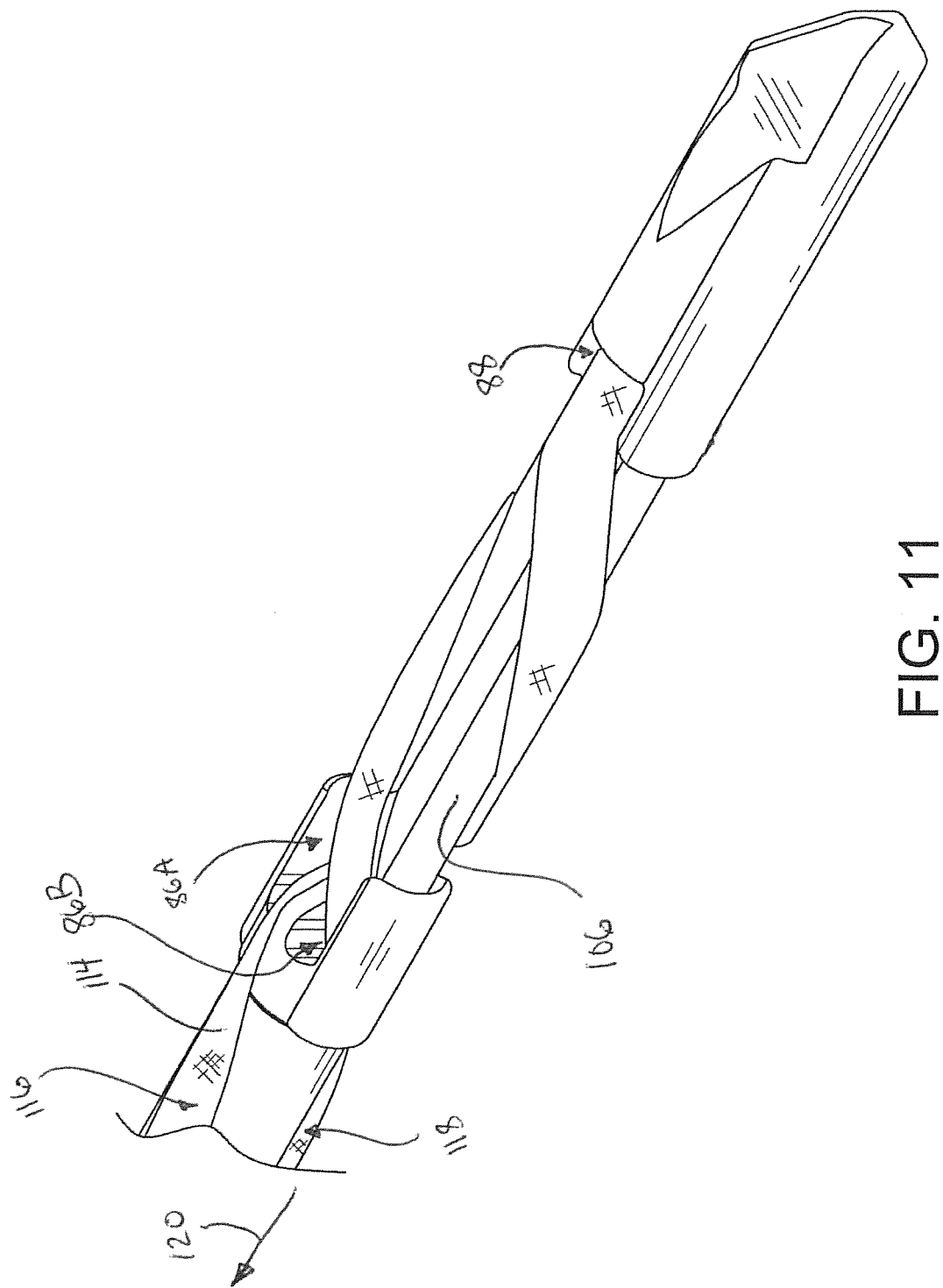
FIG. 11 is an enlarged perspective view of the distal end of the cleaning obturator of FIG. 10A with one embodiment of a cleaning swab installed on the cleaning obturator.

The swab guides 86A, 86B, 88 may be seen more clearly in the enlarged view of FIG. 10A. In this embodiment, the swab guides 86A, 86B, 88 are holes which pass through the guide rod 106. The swab guides 86A, 86B, 88 are configured to receive a swab (not shown in FIG. 10A). There are many different ways a swab could engage the swab guides 86A, 86B, 88, but one possible embodiment is illustrated in FIG. 11, where a swab 114, comprising a length of umbilical tape in this example, is passed down through the swab guide 86A, wrapped around the guide rod 106 towards the swab guide 88, passed down through the swab guide 88, wrapped back around the guide rod 106 towards the swab guide 86B, and then passed down, through the swab guide 86B. The ends of the swab 116, 118 may be routed along the guide rod 106 towards the phased handle 104 (not visible in this view).

Although the swab 114 is illustrated as passing at least 360 degrees around the guide rod 106, other embodiments may have swabs which cover a greater or lesser portion of the guide rod 106. Although not a strict requirement, a substantially spiral or helical type path is advantageous over a cylindrical swab because it creates less friction with the inner walls of the percuscopic access device 82. This can make it easier to slide and maneuver the cleaning obturator 84 within the percuscopic access device 82.

As will be discussed in more detail later in this specification, the swab 114 is moved relative to the percuscopic access device 82 to clean the distal opening 94 so that a viewing scope inserted into the percuscopic access device 82 is not as likely to get fouled by bodily fluids present in the surgical area. With a wrapped swab 114 configuration like the one illustrated in FIG. 11, one end of the swab (either end 116 or end 118) may advantageously be pulled in a proximal direction 120 (or other direction) to cause a previously used portion of the swab to move past the area between the swab guides 86A, 86B and 88 and be replaced by a clean portion of the swab 114 to improve/refresh/extend the cleaning capacity of the cleaning obturator 84. The end of the swab which is pulled may include a pull coupled to the swab to make it easier to grasp. The pull may also be configured to help a user thread the swab 114 through the one or more swab guides 86A, 86B, 88 when first setting up the swab 114 on the guide rod 106.

FIG. 12 illustrates the cleaning obturator 84 in a side view. The swab 114 can be seen wrapped around the distal end 110 of the guide rod 106, proximal to the plugging tip 112. FIG. 12A shows this in enlarged detail. The ends 116, 118 of the swab 114 are shown truncated in FIG. 12A for simplicity, but as can be seen in FIG. 12, the suture ends 116, 118 may pass along the guide rod 106 and pulled into a swab holding groove 122. The groove 122 may be better seen in the exploded view of FIG. 10.

Figure 13:
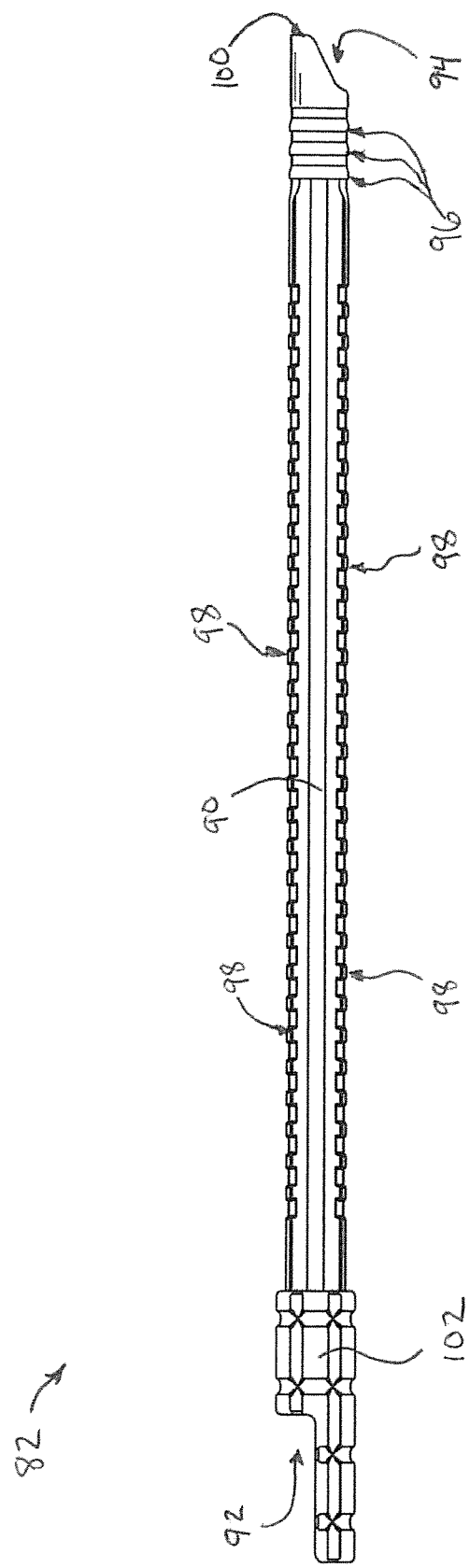
FIG. 13 is a side view of the percuscopic access device of FIG. 10.

FIG. 13 illustrates the percuscopic access device 82 in a side view. Many features of the percuscopic access device 82 have been discussed above. The one or more recesses 100 on the inside of the hollow shaft 90, in communication with the distal opening 94 are similar to recesses 40 described with respect to the previous embodiment.

FIGS. 14 and 15 are side views which illustrate two phases of interaction between the percuscopic access device 82 and the cleaning obturator 84. In FIG. 14, the cleaning obturator 84 has been inserted into the percuscopic access device 82 such that the first interface 102A of the percuscopic access device phased handle 102 is in contact with the first interface 104A of the cleaning obturator phased handle 104. In this position, or phase, the plugging tip 112 is sealing the hollow shaft 90 of the percuscopic access device 82. Although not visible on the distal end 130 in FIG. 14, the swab 114 is wrapped around the distal end of the cleaning obturator 84 as discussed previously, and the swab ends 116, 118 extend along the guide rod 106 and are held in place by passing through the notch 122. As configured in FIG. 14, the distal end 130 of the assembly may be inserted into an incision in a patient. The narrow size and atraumatic profile of the assembly are intended for minimizing iatrogenic intercostal tissue space trauma and to maintain hemostasis.

Once the distal end 130 of the assembly has been inserted into the patient, the phased handle 104 of the cleaning obturator 84 is rotated 180 degrees around a longitudinal axis, causing the first interface 104A of the cleaning obturator phased handle 104 to disengage from the first interface 102A of the percuscopic access device phased handle 102. The phased handle 104 of the cleaning obturator 84 may then be pushed in a distal direction 132 until the first interface 104A of the cleaning obturator phased handle 104 contacts the second interface 102B of the percuscopic access device phased handle 102 as shown in FIG. 15. This causes the swab 114 to clean out the distal opening 94 of the percuscopic access device 82 so that fluids do not enter this optical space. Ideally, but not necessarily, the distance along the guide rod 106 for a 360 degree wrap of the swab 114 is less than or equal to the distance the guide rod 106 travels relative to the percuscopic access device 82 when the cleaning obturator 84 is moved into the position shown in FIG. 15. This will ensure that all edges of the distal opening 94 have a chance to be cleaned.

The cleaning obturator 84 may then be removed from the percuscopic access device 82, and a viewing scope may be inserted therein. If, at any time, it is desired to clean the percuscopic access device 82 again, the viewing scope (not shown) may be removed from the percuscopic access device 82 and the cleaning obturator 84 may be inserted again as shown in FIG. 15. Additionally, the swab 114 may be advanced, as discussed above, to present a clean swab surface to the distal opening 94 for any of the ensuing cleanings.

Figure 16:
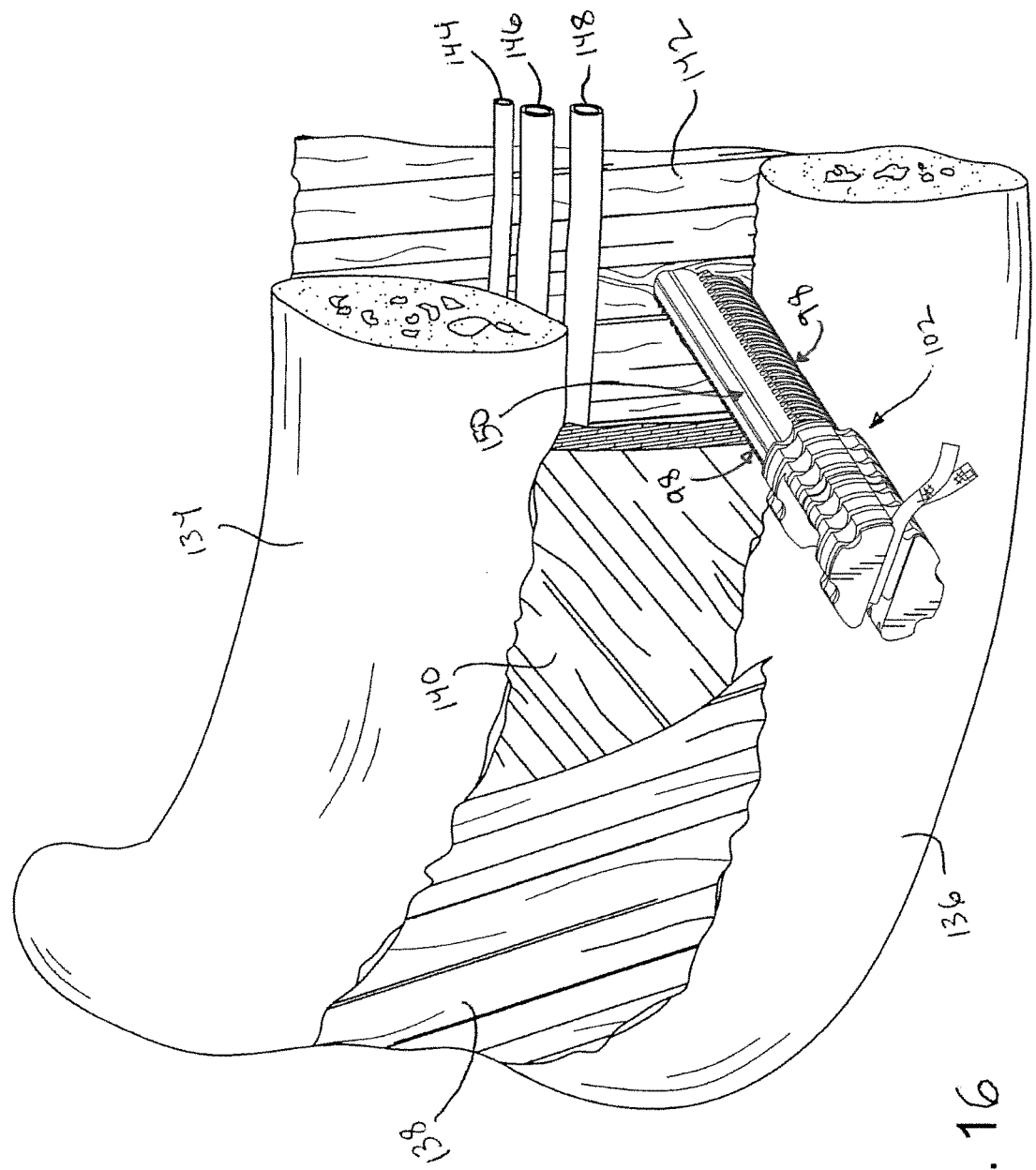
FIG. 16 is an exposed perspective view of the tissue between a pair of ribs and its interaction with the percuscopic access device inserted therein.

FIG. 16 is an exposed perspective view of the tissue between a pair of ribs 134, 136 and its interaction with the percuscopic access device 102 inserted therein. The tissue between the ribs 134, 136 includes a layer of external intercostal muscle 138, a layer of internal intercostal muscle 140, and a layer of innermost intercostal muscle 142. An intercostal vein 144, and intercostal artery 146, and an intercostal nerve 148 run along the underside of each rib. As illustrated in FIG. 16, the textured features 98 are oriented away from the ribs 134, 136 so that the textured features 98 may help grip the muscle tissue that the device 102 has been pushed through. The textured features 98 are oriented away from the ribs 134, 136 and smoother surfaces 150 (only one of which is visible in this view) located between the textured features 98 are facing the ribs 134, 136. In this orientation, the smoother surfaces 150 may tend to reduce potential damage to the vein 144, artery 146, and nerve 148 which are on the underside of the ribs 134, 136 while still allowing the textured features 98 to provide grip within the intercostal muscles 138, 140, 142.

FIGS. 17 and 18 are perspective views of another embodiment of a distal end of a cleaning obturator 152. For some embodiments, the cleaning swab may not come pre-attached with the cleaning obturator 152. To facilitate proper installation of the swab, some embodiments of the cleaning obturator 152 may be provided with one or more swab path indicators 154, 156. In the embodiment of FIGS. 17 and 18, the first swab path indicator 154 shows the desired path on which a swab threaded up through the swab guide 86B should be wrapped on until it is passed up through swab guide 88. Similarly, the second swab path indicator 156 shows the desired path on which a swab threaded up through the swab guide 88 should be wrapped on until it is passed up through swab guide 86A. The swab path indicators may be formed in a variety of ways known to those skilled in the art, including, but not limited to by etching, molding, grinding, stamping, chiseling, scratching, printing, and marking.

The devices discussed above can reduce the time it takes for a particular minimally invasive surgical procedure by preventing or reducing the fouling of viewing scopes. It can be time consuming to have to remove a viewing scope in order to clean its lens. Helping to reduce the instances of such lens cleaning may reduce the amount of time patients need to be attached to a cardio-pulmonary bypass (CPB) machine, thereby reducing the likelihood of CPB-related side effects. Faster and more reliable cardiac operations offer additional benefits, such as reduced surgical team fatigue and more efficient use of critical resources. Expediting cardiac surgery can also improve patient outcomes.

Various advantages of a percuscopic access device and cleaning obturator have been discussed above. Embodiments discussed herein have been described by way of example in this specification. It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. The percuscopic access device and the cleaning obturator may be made from a variety of materials, including, but not limited to one or more metals, alloys, or plastics. The swab may be made from a variety of materials, including, but not limited to cotton, natural fibers, synthetic fibers, and foam. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A percuscopic access device, comprising:
    a hollow shaft with a proximal opening and a distal opening;
    one or more barrier ridges on the outside of the hollow shaft, the one or more barrier ridges each interposed between one or more recesses on the outside of the hollow shaft, the barrier ridges flush with respect to the outside of the hollow shaft;
    one or more recesses on the inside of the hollow shaft and in communication with the distal opening; and
    a phased handle adjacent the proximal opening for interfacing with an obturator having a complementary phased handle, wherein the phased handle is movable between a sealing position and a cleaning position and configured such that:
    a.) a first interface of the percuscopic access device is in contact with a first interface of the obturator when in the sealing position; and
    b.) the first interface of the percuscopic access device is in contact with a second interface of the obturator when in the cleaning position.

2. The percuscopic access device of claim 1, wherein the proximal opening is substantially the same diameter as the distal opening.

3. The percuscopic access device of claim 1, wherein the hollow shaft comprises at least a partially beveled end where the distal opening is located.

4. The percuscopic access device of claim 1, further comprising:
    one or more textured features on the outside of the hollow shaft.

5. The percuscopic access device of claim 4, wherein the one or more barrier ridges are located distal to the one or more textured features.

6. The percuscopic access device of claim 1, wherein at least one of the one or more barrier ridges fully encircles the hollow shaft.

7. The percuscopic access device of claim 1, wherein at least one of the one or more barrier ridges comprises a hydrophilic material.

8. The percuscopic access device of claim 1, wherein at least one of the one or more barrier ridges comprises a hydrophilic coating.

9. The percuscopic access device of claim 1, wherein at least one of the one or more barrier ridges is protruding with respect to the outside of the hollow shaft.

10. The percuscopic access device of claim 1, wherein the one or more recesses on the inside of the hollow shaft comprise a hydrophilic coating.

11. The percuscopic access device of claim 1, further comprising one or more protrusions on the inside of the hollow shaft which help to define at least one of the one or more recesses.

12. The percuscopic access device of claim 11, wherein the one or more protrusions are substantially longitudinal protrusions.

13. The percuscopic access device of claim 11, wherein the one or more protrusions only extend partway into the inside of the hollow shaft.

14. The percuscopic access device of claim 11, wherein the one or more protrusions comprise a ramped transition from an inside diameter of the hollow shaft to a smaller effective diameter.

15. A cleaning obturator, comprising:
   a guide rod having a proximal end and a distal end;
   a plugging tip on the distal end; and
   one or more swab guides, wherein the one or more swab guides pass through the guide rod and are proximal to the plugging tip;
   and wherein the one or more swab guides are configured to slideably receive a swab.

16. A cleaning obturator, comprising:
   a guide rod having a proximal end and a distal end;
   a plugging tip on the distal end;
   one or more swab guides, wherein the one or more swab guides pass through the guide rod and are proximal to the plugging tip; and
   a swab configured for slideable engagement with the one or more swab guides.

* * * * *